(12) United States Patent
Xiao et al.

(10) Patent No.: US 6,329,181 B1
(45) Date of Patent: Dec. 11, 2001

(54) HELPER FUNCTIONS FOR RECOMBINANT VECTOR PRODUCTION

(75) Inventors: Weidong Xiao, Jenkintown; Matthew J. During; Lei Cao, both of Philadelphia, all of PA (US)

(73) Assignee: Neurologix, Inc., Great Neck, NY (US)

( * ) Notice: Subject to any disclaimer, the term of this patent is extended or adjusted under 35 U.S.C. 154(b) by 0 days.

(21) Appl. No.: 09/633,566

(22) Filed: Aug. 7, 2000

(51) Int. Cl.$^7$ ............... C12N 15/63; C12N 15/64; C12N 15/864; C07H 21/04
(52) U.S. Cl. .................. 435/91.41; 435/235.1; 435/320.1; 435/69.1; 435/455; 435/456; 435/457; 435/325; 435/366; 435/91.4; 536/23.1; 536/23.72; 536/24.1; 536/24.2
(58) Field of Search .................. 435/235.1, 320.1, 435/69.1, 455, 456, 457, 325, 366, 91.4, 91.41; 536/23.1, 23.72, 24.1, 24.2

(56) References Cited

U.S. PATENT DOCUMENTS

| | | | |
|---|---|---|---|
| 5,436,146 | * 7/1995 | Shenk et al. | 435/457 |
| 5,585,254 | 12/1996 | Maxwell et al. | 435/465 |
| 5,756,283 | 5/1998 | Wilson et al. | 435/5 |
| 5,853,716 | 12/1998 | Tattersall et al. | 424/93.2 |
| 5,945,335 | 8/1999 | Colosi | 435/369 |
| 6,001,650 | 12/1999 | Colosi | 435/369 |
| 6,027,931 | 2/2000 | Natsoulis et al. | 435/235.1 |

OTHER PUBLICATIONS

Robert M. Kotin, "Prospects for the Use of Adeno–Associated Virus as a Vector for Human Gene Therapy", (1994), Human Gene Therapy 5:793–801.*

Allen, J. et al., "Identification and Elimination of Replication–Competent Adeno–Associated Virus (AAV) That Can Arise by Nonhomologous Recombination during AAV Vector Production," J Virol 1997 Sep;71(9):6816–22.

Flotte, T. et al., "An Improved System for Packaging Recombinant Adeno–Associated Virus Vectors Capable of in Vivo Transduction," Gene Ther 1995 Jan;2(1);29–37.

Grimm, D. et al., "Progress in Adeno–Associated Virus Type 2 Vector Production: Promises and Prospects for Clinical Use," Hum Gene Ther 1999 Oct 10;10(15):2445–50.

Li, J. et al., "Role for Highly Regulated rep Gene Expression in Adeno–Associated Virus Vector Production," J Virol 1997 Jul;71(7):5236–43.

Wang, X. et al., "Characterization of Wild–Type Adeno–Associated Virus Type 2–Like Particles Generated During Recombinant Viral Vector Production and Strategies for Their Elimination," J. Virol 1998 Jul;72(7):5472–80.

* cited by examiner

Primary Examiner—David Guzo
(74) Attorney, Agent, or Firm—Thomas J. Engellenner; Nutter, McClennen & Fish LLP (57) ABSTRACT

The present invention provides methods and compositions for preparations of recombinant parvovirus virions with a reduced number of replication competent particles. The compositions of the present invention include nucleic acids encoding parvovirus helper functions which contain at least one non-native intron sequence. The present invention also includes helper function vectors, host cells transfected with the helper function vectors, methods of using the helper function vectors, and recombinant parvovirus virions produced by such methods.

45 Claims, 5 Drawing Sheets

HELPER FUNCTIONS FOR RECOMBINANT VECTOR PRODUCTION

BACKGROUND OF THE INVENTION

The present invention provides methods, host cells, and vectors which permit efficient production of recombinant parvovirus virions. In particular, the present invention relates to parvovirus helper functions that provide for high-efficiency recombinant parvovirus production but reduce the potential of generating replication competent particles.

Parvoviruses vectors, such as adeno-associated virus (AAV) vectors are useful for gene therapy. In general, recombinant adeno-associated virus (rAAV) vectors are generated by transfection of an AAV vector plasmid and a helper plasmid in the presence of helper virus infection (Samulski, et al. (1989) *J Virol* 63: 3822–3828). The AAV vector is constructed by replacing the whole coding region of the AAV genome with a transgene. This creates a defective AAV vector which is incapable of replication. In order to provide the necessary helper functions, a helper plasmid can be constructed. The helper plasmid contains the AAV Cap and/or Rep coding region, but lacks the AAV inverted terminal repeat sequences. Accordingly, the helper plasmid can neither replicate nor package itself. After the AAV helper plasmid and the AAV vector are introduced into a host cell, the transfected cells can be infected with a helper virus, for example, an adenovirus, which, among other functions, transactivates the AAV promoters present on the helper plasmid that direct the transcription and translation of AAV Rep and Cap regions. Upon subsequent culture of the host cells, recombinant AAV virions (harboring the transgene) are produced.

Although there is no overlapping sequence between the AAV vector and the helper plasmid, the probability of generating replication competent AAV (rcAAV) particles through non-homologous recombination, is relatively high (Allen et al. (1997) *J Virol* 71: 6816–6822). These replication competent particles affect transgene expression (Grimm, et al. (1999) *Hum Gene Ther* 10: 2445–2450), are a safety hazard in applications of AAV vectors for human gene therapy, and also reduce the yield of recombinant AAV virions.

Previous attempts to address the problem of rcAAV particles includes using heterologous promoters for driving the Rep coding and Cap region, separating the Cap and Rep coding regions into different vectors (See Allen, et al. (1997) J Virol 71: 6816–6822 and Flotte, et al. (1995) *Gene Ther* 2: 29–37), and using truncated AAV terminal repeat sequences (Wang, et al. (1998) *J Virol* 72: 5472–5480). Although these approaches reduced the number of replication competent particles, the replication competent particles were still present in large scale preparations. Accordingly, a need exists for methods and compositions of producing recombinant viral vectors without the presence for contaminating replication competent particles. A need also exists for methods of producing recombinant AAV virions without the presence of contaminating replication competent particles.

SUMMARY OF THE INVENTION

The present invention is based on the discovery that recombinant parvovirus virions can be produced at a higher titer, and without detectable quantities of replication competent particles, using the helper functions of the invention. The helper functions comprise at least one intron sequence inserted at one or more positions within a non-structural coding region, and/or a structural coding region of a parvovirus genome. The intron sequences can be non-native intron sequences, which are not typically present in a parvovirus genome, for example, a β-globin intron sequence. The intron sequence can be a native intron sequence that is typically present in a parvovirus. At least one native intron sequence can be inserted at one or more positions within the non-structural coding region and/or the structural coding region of a parvovirus genome. The invention also encompasses inserting a combination of a native intron sequence and a non-native intron sequence in at least one or more positions within the non-structural coding region and/or the structural coding region of a parvovirus genome. The technology described herein enables the rapid and efficient generation of recombinant parvovirus virions with a reduced titer, or without the presence of detectable replication competent particles. In particular, the invention provides nucleic acid molecules that encode parvovirus helper functions containing at least one native and/or non-native intron sequence, and methods for producing recombinant parvovirus virions using such helper functions.

The intron sequence can be inserted into one or more positions in a non-structural protein coding region, for example, the Rep coding region. The intron sequence can be inserted into one or more positions in a structural protein coding region, for example, the Cap coding region, or any combination thereof. Introduction of at least one intron sequence to the structural and/or non-structural protein coding regions reduces and/or eliminates the number of contaminating replication competent particles generated during recombinant viron production.

Accordingly, in one aspect, the invention features a nucleic acid molecule encoding a parvovirus helper function. The nucleic acid molecule comprises a non-structural protein coding region derived from a parvovirus, a structural protein coding region derived from a parvovirus, and at least one intron sequence inserted at one or more positions within said regions, such that the intron sequence increases the size of the nucleic acid molecule to a size larger than a nucleic acid molecule without the intron sequence, wherein the increase in size prevents packaging of a pseudo wild-type parvovirus into a replication competent particle.

In one embodiment, the nucleic acid molecule encoding a parvovirus helper function is an adeno-associated virus selected from the group consisting of AAV-1, AAV-2, AAV-3, AAV-4, AAV-5 and AAV-6, preferably, AAV-2. The non-structural protein can be a protein such as a Rep protein and the structural protein can be a Cap protein. Intron sequences are inserted to increase the size of the viral genome. In one embodiment, the intron sequence can be at least one non-native intron sequence i.e., an intron sequence that is not typically found in the viral genome. Examples of non-native sequences include, but are not limited to, α-globulin intron, β-globulin intron, collagen intron, ovalbumin intron, SV40 intron and p53 intron. The non-native intron sequence can also be derived from an autonomous parvovirus such as, LUIII, minute virus of mice (MVM), human parvovirus B19, hamster parvovirus, feline panleukopenia virus, canine parvovirus porcine parvovirus, latent rat parvovirus and mink enteris parvovirus. In another embodiment, the intron sequence can be a native intron sequence, which is typically present in the parvoviral genome, i.e., at least one intron sequence that is typically found in the parvovirus.

A particularly useful parvovirus is AAV-2, accordingly the invention features helper functions that contain nucleic acids encoding the Rep and/or the Cap proteins for AAV-2 with at least one intron sequence. In a helper function with a nucleic acid encoding both the Cap and the Rep proteins, at least one intron sequence can be inserted into the nucleic acid encoding the Cap coding region, the Rep coding region, or both the Cap coding region and the Rep coding regions.

Accordingly, in one aspect, the invention features a nucleic acid molecule encoding an adeno-associated virus (AAV) helper function. The nucleic acid comprises a Rep coding region derived from an AAV, a Cap coding region derived from an AAV, and at least one intron sequence inserted at one or more positions within the Cap coding region and the Rep coding region, such that the intron sequence increases the size of the nucleic acid molecule to a size larger than a nucleic acid molecule without the intron sequence, wherein the increase in size prevents packaging of a pseudo wild-type AAV into a replication competent particle.

The invention also features a helper function containing a nucleic acid with either a Cap coding region, or a Rep coding region into which at least one intron sequence is inserted. This helper function can be co-transfected into a host cell with a second helper function comprising a nucleic acid with Rep coding region, or a Cap coding region, respectively.

Accordingly, in another aspect, the invention features a nucleic acid molecule encoding an adeno-associated virus (AAV) helper function. The nucleic acid molecule comprises a Cap coding region derived from an AAV, and at least one intron sequence inserted at one or more positions within the Cap coding region, such that the intron sequence increases the size of the nucleic acid molecule to a size larger than a nucleic acid molecule without the intron sequence wherein the increase in size prevents packaging of a pseudo wild-type AAV into a replication competent particle.

In another aspect, the invention features a nucleic acid molecule encoding an adeno-associated virus (AAV) helper function. The nucleic acid molecule comprises a Rep coding region derived from an AAV, and at least one intron sequence inserted at one or more positions within the Rep coding region, such that the intron sequence increases the size of the nucleic acid molecule to a size greater than a nucleic acid molecule without the intron sequence, wherein the increase in size prevents packaging of a pseudo wild-type AAV into a replication competent particle.

The present invention also provides parvovirus helper function vectors that express gene products encoded by the parvovirus helper function vectors. Such vectors may be constructed by linking the nucleic acid molecules of the present invention with suitable control sequences that direct the replication and expression of the resulting parvovirus helper function vectors. The helper function vector can also further comprise one or more accessory function genes and/or accessory regulation elements. Examples of suitable helper function vectors include, but are not limited to, adenovirus, herpesvirus and baculovirus. In a preferred embodiment, the helper function vector is a plasmid.

In yet another aspect, the invention features a method of producing recombinant parvovirus virions by introducing a parvovirus vector into a host cell, adding a parvovirus helper function vector into the host cell. The parvovirus helper function vector comprises a nucleic acid molecule encoding a non-structural protein region and a structural protein region derived from a parvovirus, and at least one intron sequence inserted at one or more positions in the regions, such that the intron sequence increases the size of the nucleic acid molecule to a size larger than a nucleic acid molecule without the intron sequence, wherein in the increase in size prevents packaging of a pseudo wild-type parvovirus into a replication competent particle; and culturing the host cell to produce recombinant parvovirus virions.

In another aspect, the invention features a method of producing recombinant AAV virious by introducing a AAV vector into a host cell, adding a helper function vector into the host cell. The helper function vector comprises a nucleic acid molecule with a Cap coding region and a Rep coding region derived from an AAV, and at least one intron sequence inserted at one or more positions in the Cap coding region and the Rep coding region, such that the intron sequence increases the size of the nucleic acid molecule to a size larger than a nucleic acid molecule without the intron sequence, wherein the increase in size prevents packaging of a pseudo wild-type AAV into a replication competent particle, and culturing the host cell to produce recombinant AAV virions.

The AAV vector can be selected from the group consisting of AAV-1, AAV-2, AAV-3, AAV4, AAV-5 and AAV6. The helper function vector can comprise a nucleic acid molecule with a Cap coding region and a Rep coding region derived from an AAV selected from the group consisting of AAV-1, AAV-2, AAV-3, AAV4, AAV-5 and AAV-6. The intron sequence can be a non-native intron sequence, a native AAV intron sequence, or a combination thereof. The helper function can be provided in a helper function vector, which include, but are not limited to a plasmid, phage, transposon, cosmid, and virus.

In another aspect, the invention features a method of producing recombinant AAV virious by introducing an AAV vector into a host cell, adding a first helper function vector into the host cell. The first helper function vector comprises a nucleic acid molecule encoding an AAV region selected from the group consisting of a Cap coding region and a Rep coding region, and at least one intron sequence inserted in at least one position within said regions, such that the intron sequence increases the size of the nucleic acid molecule to a size larger than a nucleic acid molecule without the intron sequence, werein the increase in size prevents packaging of a pseudo wild-type AAV into a replication competent particle, and culturing the host-cell to produce recombinant AAV virions.

In one embodiment, the method can further comprise introducing a second helper function vector into a host cell. The second helper function vector comprises a nucleic acid molecule encoding an AAV region selected from the group consisting of a Cap coding region and a Rep coding region, and the second helper function vector is different from the first helper function vector. The second helper function having nucleic acid molecules without the additional intron sequence.

In another embodiment, the method can further comprise introducing a second helper function vector into a host cell. The second helper function vector comprises a nucleic acid molecule encoding an AAV region selected from the group consisting of a Cap coding region and a Rep coding region, and an intron sequence inserted in at least one position in said regions, wherein the second helper function vector is different from the first helper function vector. The first and second helper functions can comprise a nucleic acid molecule encoding an AAV region derived from an AAV selected from the group consisting of AAV-1, AAV-2, AAV-3, AAV4, AAV-5 and AAV-6. The invention also features recombinant parvovirus virions and AAV virions produced by the claimed methods.

DETAILED DESCRIPTION

The present invention is based on the discovery that recombinant virions (e.g. parvovirus virions) can be produced at a higher titer, and without detectable quantities of replication competent particles, using the helper functions of the invention. The helper functions comprise at least one intron sequence inserted at one or more positions within a structural protein coding region, and/or a non-structural protein coding region of a parvovirus genome. The technology described herein enables the rapid and efficient generation of recombinant virions with a reduced titer, or without the presence of replication competent particles.

So that the invention is more clearly understood, the following terms are defined:

The term "nucleic acid molecule" as used herein refers to a nucleotide sequence, e.g., DNA or RNA.

The term "intron sequence" or "intron" or "intronic sequence" as used herein refers to the art recognized use of the term for a segment of DNA that is transcribed, but which is removed from within the transcript by splicing processes which splice together the sequences on either side of it. The sequences of DNA comprising an interrupted gene are divided into two categories, exons and introns. Exons are the regions that are represented in the mRNA, while introns are regions that are missing from the mRNA. The presence of introns creates genes that are much longer than their coding regions.

The term "native intron sequence" refers to a wild-type intron sequence present in a non-structural coding region or a structural coding region of a parvovirus. For example, AAV-2 has one 315 base pair native intron sequence present in the structural coding region of the genome. A helper function construct comprising a parvovirus non-structural protein coding region and/or structural coding region can have one or more additional native intron sequences inserted into one or more positions within the non-structural protein coding region and/or the structural coding region. For example, an additional 315 base pair native intron of AAV-2 can be inserted into one or more positions of the AAV-2 Cap coding region, Rep coding region, or both the Cap coding region and the Rep coding region.

The term "non-native intron sequence" as used herein refers to an intron sequence that is not typically present in a parvovirus genome. A non-native intron sequence can be a known intron sequence derived from any organism other than the parvovirus. For example, a non-native intron sequence can be an intron sequence from humans, chimpanzees, apes, monkey, sheep, pigs, goats, horses, dogs, cats, mice, rats, guinea pigs, adenovirus, herpesvirus, vaccinia virus, and the like. A helper function construct comprising a parvovirus non-structural protein coding region and/or a structural protein coding region can have at least one non-native intron sequence inserted into one or more positions within the non-structural coding region and/or the structural coding region.

The term "helper function" as used herein refers to complemented functions that are missing from a parvovirus vector. The helper function can be provided in any form that allows the parvovirus vector to use the missing functions. The nucleic acid molecule encoding the helper function can have at least one native intron sequence inserted into one or more positions of the structural protein coding region, the non-structural protein coding region, or both the structural and non-structural protein coding region. The helper function can have at least one additional native intron sequence inserted into one or more positions of the structural protein coding region, the non-structural protein coding region, or both the structural and non-structural protein coding region. Also within the scope of the invention are helper functions comprising a combination of native and non-native intron sequences.

The term "AAV helper functions" as used herein refers to AAV-derived coding sequences which can be expressed to provide AAV protein products that, in turn, function in trans for productive AAV replication. Contemporary recombinant AAV (rAAV) virion production involves co-transfection of a host cell with an AAV vector plasmid and a construct which provides AAV helper functions to complement functions missing from the AAV vector plasmid. In this manner, the host cell is capable of expressing the AAV proteins necessary for AAV replication and packaging. The host cell can also be infected with a helper virus to provide accessory functions. The helper virus is generally an infectious adenovirus (type 2 or 5), or herpesvirus.

AAV helper functions can be provided for example, by an AAV helper plasmid that includes the AAV Rep and/or Cap coding regions but which lacks the AAV ITRs. Accordingly, the helper plasmid can neither replicate nor package itself. A number of vectors that contain the Rep coding region are known, including those vectors described in U.S. Pat. No. 5,139,941, having ATCC Accession Numbers 53222, 53223, 53224, 53225 and 53226. Similarly, methods of obtaining vectors containing the HHV-6 homologue of AAV Rep are described in Thomson et al. (1994) *Virology* 204:304–311. A number of vectors containing the Cap coding region have also been described, including those vectors described in U.S. Pat. No. 5,139,941. Thus, AAV helper functions include both of the major AAV open reading frames (ORFs), Rep and Cap. AAV helper functions are used herein to complement AAV functions in trans that are missing from AAV vectors. The nucleic acid molecule encoding the AAV helper function can have at least one non-native intron sequences inserted into one or more positions in the Cap coding region, in the Rep coding region, or in both the Cap and Rep coding region. The nucleic acid molecule encoding the AAV helper function can have at least one native intron sequence inserted at one or more positions in the Cap coding region, the Rep coding region, or in both the Rep and Cap coding region. Also within the scope of the invention are AAV helper functions comprising a combination of native and non-native intron sequences. The native or non-native intron sequences will be spliced out during transcription and translation of the mRNA. The purpose of the native or non-native intron sequences inserted into the helper functions is to increase the size of the helper function such that during non-homologous recombination events, the resulting pseudo wild type parvovirus has a genome size much larger than the wild type parvovirus. The increase in genome size in the pseudo wild type parvovirus prevents its efficient packaging into replication competent particles thereby reducing the number of pseudo-wild type replication competent particles.

The term "AAV helper construct" as used herein refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV Rep and/or Cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. In a preferred embodiment, the helper function is provided as a helper plasmid. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) J. Virol. 65:2936–2945. A number of other vectors have been described which encode Rep and/or Cap expression products. See, e.g., U.S. Pat. No. 5,139,941.

The term "vector" as used herein refers to a genetic element, such as a plasmid, phage, transposon, cosmid, chromosome, virus, virion, and the like, which is capable of replication when associated with the proper control elements and which can transfer gene sequences into cells. Thus, the term includes cloning and expression vehicles, as well as viral vectors. A vector is used to "carry" inserted foreign DNA.

The term "AAV vector" as used herein refers to a vector derived from an adeno-associated virus serotype, including but not limited to, AAV-1, AAV-2, AAV-3, AAV4, AAV-5, AAV-6, AAVX7, and the like. AAV vectors can have one or more of the AAV wild-type coding regions deleted in whole or in part, preferably the Rep and/or Cap coding regions, but retain functional flanking Inverted Terminal Repeat (ITR) sequences. Functional ITR sequences permit the rescue, replication and packaging of an AAV virion. Thus, an AAV vector is defined herein to include at least those sequences required for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

The term "recombinant virus" as used herein refers to a virus that has been genetically altered, e.g., by the addition or insertion of a heterologous nucleic acid construct into the particle.

The term "virion" as used herein refers to an infectious agent comprising a genome encapsulated in a protein coat.

The term "recombinant virion," as used herein refers to an infectious, replication-defective virus composed of a viral coat, encapsidating a transgene which is flanked on both sides by viral ITRs. For example, the recombinant virion can be a recombinant AAV virion (rAAV virion). A recombinant AAV virion can be produced in a suitable host cell which has had an AAV vector, AAV helper functions and/or accessory functions introduced therein. In this manner, the host cell is rendered capable of encoding AAV capsid proteins that are required for packaging the AAV vector (containing a transgene) into recombinant AAV virions for subsequent gene delivery.

The term "AAV virion" as used herein refers to a complete virus particle, wild-type AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

The term "replication competent particle" refers to a recombinant pseudo wild-type virus that has been packaged and is capable of infected and replicating in a host. Replication competent particles are typically produced during recombinant virion production, and arise due to non-homologous recombination events. These non-homologous recombination events result in the exchange of genetic material between the viral vector (e.g., an AAV vector comprising a transgene flanked 3' and 5' by ITR's) and a helper plasmid, (e.g., an adenovirus with the AAV Rep and Cap coding regions). During non-homologous recombination events, the transgene sequence of the vector is exchanged for the Cap and Rep coding region in the helper plasmid. This results in the production of pseudo wild-type replication competent viruses comprising the ITR's and the Rep/Cap coding regions. These pseudo wild-type viruses are capable of being packaged onto a replication competent particles.

The term "pseudo-wild type parvovirus" as used herein refers to a parvovirus produced by non-homologous recombination events after a parvovirus vector is co-transfected with a helper construct carrying the Rep and Cap genes. The resulting pseudo-wild type parvovirus has the Rep and Cap genes sandwiched between the parvovirus ITR's and is capable of being packaged into a replication competent particle.

The term "structural coding region" as used herein refers to a nucleotide sequence from a parvovirus genome that encodes for structural proteins, such as the capsid proteins.

The term "non-structural coding region" as used herein refers to a nucleotide sequence from a parvovirus genome that encodes for non-structural proteins, such as NS1 protein.

The term "AAV Rep coding region" as used herein refers to the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome. For a description of the AAV rep coding region, see, e.g., Muzyczka (1992) *Current Topics in Microbiol. and Immunol.* 158:97–129; and Kotin (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311).

The term "AAV Cap coding region" as used herein refers to the art-recognized region of the AAV genome which encodes one or more capsid proteins VP1, VP2, and VP3, or functional homologues thereof. These cap expression products supply the packaging functions which are collectively required for packaging the viral genome. For a description of the AAV cap coding region, See, e.g., Muzyczka (Supra).

The term "accessory functions" as used herein refers to non-AAV derived viral and/or cellular functions upon which AAV is dependent for its replication. Thus, the term captures proteins and RNAs that are required in AAV replication, including those moieties involved in activation of AAV gene transcription, stage specific AAV MRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus. For example, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, (1992) *Curr. Topics. Microbiol. and Immun.* 158:97–129. Specifically, early adenoviral gene regions E1a, E2a, E4, VAI RNA and, possibly, E1b are thought to participate in the accessory process. Janik et al. (1981) *Proc. Nati. Acad. Sci. USA* 78:1925–1929. Herpesvirus-derived accessory functions have been described. See, e.g., Young et al. (1979) *Prog. Med. Virol.* 25:113. Vaccinia virus-derived accessory functions have also been described. See, e.g., Carter, (1990), supra., Schlehofer et al. (1986) *Virology* 152:110–117. Accessory functions can be provided an "accessory function vector." An accessory function vector can be transfected into a suitable host cell, wherein the vector is then capable of supporting AAV virion production in the host cell. Examples of accessory function vectors include, but are not limited to, plasmid, phage, transposon or cosmid.

The term "autonomous parvoviruses" refers to the art recognized use of the term for small DNA viruses that replicate autonomously in rapidly dividing cells. Autonomous parvovirus genomes are single-stranded DNA molecules about 5 kilobases (kb) in size. The genomes are organized such that the gene encoding the nonstructural polypeptides NS1 and NS2 is located on the left side of the genome and the gene encoding the structural polypeptides required for capsid formation are on the right side of the genome. Autonomous parvovirus genomes also have inverted repeat sequences at each end which contain essential signals for replication and encapsidation of the virus. Studies on the mechanistics of autonomous parvovirus replication, gene expression, encapsidation, and cytotoxicity are described by Sinkovics (1989) *Anticancer Res.* 9: 1281–1290. Examples of autonomous parvoviruses include, but are not limited to, LuIII parvovirus, minute virus of mice (MVM), hamster parvovirus, feline panleukopenia virus, canine parvovirus, porcine parvovirus, latent rat virus, mink enteritis virus, human parvovirus, bovine parvovirus, and Aleutian mink disease parvovirus nucleic acid sequences. Preferred autonomous parvoviruses are the LuIII parvovirus and the MVM parvovirus.

The term "transgene", as used herein refers refer to gene sequences. Transgenes, or gene sequences, can be derived from a variety of sources including DNA, cDNA, synthetic DNA, and RNA. Such transgenes can comprise genomic DNA which may or may not include naturally occurring introns. Moreover, such genomic DNA may be obtained in association with promoter regions or poly A sequences. Genomic DNA or cDNA may be obtained by means well known in the art. A transgene may be any gene sequence whose expression produces a gene product that is to be expressed in a cell. A gene can include, but is not limited to, cDNA from prokaryotic or eukaryotic mRNA, genomic DNA sequences from prokaryotic or eukaryotic DNA, and even synthetic DNA sequences. The gene product may affect the physiology of the host cell. Alternatively the transgene may be a selectable marker gene or reporter gene. The transgene can be operably linked to a promoter or other regulatory sequence sufficient to direct transcription of the transgene. Suitable promoters include, for example, as human CMV IEI promoter or an SV40 promoter.

The term "regulatory elements" is art-recognized and includes control elements such as promoters, enhancers and other expression control elements (e.g., polyadenylation signals), transcription termination sequences, upstream regulatory domains, origins of replication, internal ribosome entry sites ("IRES"), enhancers, enhancer sequences, post-regulatory sequences and the like, which collectively provide for the replication, transcription and translation of a coding sequence in a recipient cell. Not all of these regulatory elements need always be present so long as the selected coding sequence is capable of being replicated, transcribed and translated in an appropriate host cell. Such regulatory elements are known to those skilled in the art and are described in Goeddel, *Gene Expression Technology: Methods in Enzymology* 185, Academic Press, San Diego, Calif. (1990). It should be understood that the design of the viral vector may depend on such factors as the choice of the host cell to be transfected and/or the amount of protein to be expressed.

The term "promoter" is used herein refers to the art recognized use of the term of a nucleotide region comprising a regulatory sequence, where the regulatory sequence is derived from a gene which is capable of binding RNA polymerase and initiating transcription of a downstream (3'-direction) coding sequence.

The term "operably linked" as used herein refers to an arrangement of elements where the components are configured so as to perform their usual function. Thus, control elements operably linked to a coding sequence are capable of effecting the expression of the coding sequence. The control elements need not be contiguous with the coding sequence, so long as they function to direct the expression of the coding sequence. For example, intervening untranslated yet transcribed can be present between a promoter sequence and the coding sequence and the promoter sequence can still be considered "operably linked" to the coding sequence.

The terms "5'", "3'", "upstream" or "downstream" are art recognized terms that describe the relative position of nucleotide sequences in a particular nucleic acid molecule relative to another sequence.

The term "coding region" or "coding sequence" as used herein refers to a nucleic acid molecule which is transcribed (in the case of DNA) and translated (in the case of MRNA) into a polypeptide in vitro or in vivo when placed under the control of appropriate regulatory sequences.

The term "transfection" is used herein refers to the uptake of an exogenous nucleic acid molecule by a cell. A cell has been "transfected" when exogenous nucleic acid has been introduced inside the cell membrane. A number of transfection techniques are generally known in the art. See, e.g., Graham et al. (1973) *Virology,* 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous nucleic acid molecules into suitable host cells. The term refers to both stable and transient uptake of the nucleic acid molecule.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

Further details of the invention are described in the following sections:

I. Introns

The invention features nucleic acid molecules encoding parvovirus helper functions and methods of producing recombinant parvovirus virions with a low number of replication competent particles, using the helper functions of the invention. Nucleic acid molecules encoding the helper functions contain at least one intron sequence inserted within one or more positions of a non-structural protein coding region and/or a structural protein coding region derived from a parvovirus genome. The introns sequence can be a native intron sequence or a non-native intron sequence.

Most eukaryotic genes are discontinuous and consist of coding sequences (exons) interrupted by non-coding sequences (introns). After transcription into RNA, the introns are removed by splicing to generate the mature messenger RNA (mRNA). Structural features of introns and the underlying splicing mechanisms form the basis for classification of different kinds of introns. The major categories of introns are group I, group II, nuclear pre-mRNA, and tRNA introns, based on differentiated splicing mechanisms. The nucleic acid molecules and sequence methods of the invention are not limited to any particular non-native intron sequence or class of non-native intron sequence. By way of example, the non-native intron sequences can be selected from group I, group II, group III or nuclear pre-mRNA introns. Furthermore, in light of advancements made in delineating the critical and dispensable elements in each of the classes of introns, the present invention can also be practiced with portions of introns.

In one embodiment, the invention uses group I intron sequences, which can be found, for example, lower eukaryotes (e.g., *Tetrahymena thermophila* and *Physarum polycephalum*), in chloroplast, yeast, and fungal mitochondrial rRNA genes; in certain yeast and fungal mitochondrial mRNA; and in several chloroplast tRNA genes in higher plants. Group I introns are characterized by a linear array of conserved sequences and structural features.

In another embodiment, Group II introns are used, these introns are classed together on the basis of a conserved secondary structure, and have been identified in certain organellar genes of lower eukaryotes and plants. In another embodiment, eukaryotic nuclear pre-mRNA introns are used, those have conserved features that are restricted to short regions at or near the splice junctions. These pre-mRNA intron sequences can be found in yeast and have motifs such as (i) a conserved hexanucleotide at the 5' splice, (ii) an invariant heptanucleotide, the UACUAAC Box, surrounding the branch point A, (iii) a generally conserved enrichment for pyrimidine residues adjacent to the invariant AG dinucleotide at the 3' splice site. Several examples of intron sequences are available from GenBank. Preferred examples of intron sequences include, but are not limited to, α-globulin intron, β-globulin intron, collagen intron, SV/40 intron and p53 intron. In one embodiment, the helper function comprises nucleic acid molecules encoding the Rep and Cap proteins of AAV.

One or more intron sequences may be introduced into the Cap coding region, the Rep coding region, or in both the Cap coding and Rep coding regions. Furthermore, any combination of intron sequences can be inserted into one or more positions. For example, one or more β-globulin intron sequences can be introduced into the Rep coding region, and one or more collagen introns can be introduced into the Cap coding region. In another example, one β-globulin intron sequence and one collagen intron sequence can be inserted into the Rep coding and no introns are inserted into the Cap coding region, or another intron sequence that is different from the β-globulin and collagen intron sequence can be inserted into the Cap coding region. In a preferred embodiment, the AAV genome includes at least one β-globulin intron sequence and at least one collagen intron sequence. Introduction of the intron sequence into the helper function vectors comprising a non-structural protein coding region and/or a structural protein coding region results in these regions being larger than wild type parvovirus structural and non-structural protein coding regions. This increase in size appears to reduce the efficiency of packaging of the pseudo wild type virus into replication competent particles. This is exemplified in Example 2. The addition of the 850 bp human β-globin intron into the AAV genome reduced the number of replication competent particles produced. (See Table 1).

In another embodiment, artificial intron sequences can also be used in the helper functions of the invention. Artificial intron sequences can be produced using standard oligonucleotide synthesis procedures. The articifical sequences can be created by aligning known intron sequence, determining the regions of high homology between the aligned sequences and producing artificial intron sequences that contain the regions of high homology.

A helper function vector of the invention with a Rep coding region comprises at least one intron sequence inserted within the Rep coding region. The intron sequence can be a native intron sequence or a non-native intron sequence. In another embodiment, the Rep coding region comprising at lest one native intron sequence and at least one non-native intron sequence. The AAV Rep coding region of the AAV genome encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome.

A helper function vector of the invention with a Cap coding region comprises at least one intron sequence inserted within the Cap coding region. The intron sequence can be a native intron sequence or a non-native intron sequence. In another embodiment, the Cap coding region comprises at least one native intron sequence and at least one non-native intron sequence. The AAV Cap coding region of the AAV genome encodes the capsid proteins VP1, VP2, and VP3, or functional homologues thereof. AAV helper functions can be introduced into the host cell by transfecting the host cell with an AAV helper construct either prior to, or concurrently with, the transfection of the AAV vector comprising the transgene.

In one embodiment of the invention a host cell comprising a Rep coding region can be transfected with a helper function vector comprising a Cap coding region without at least one intron sequence inserted within the Cap coding region. In another embodiment, the host cell comprises a Cap coding region can be transfected with a helper function vector comprising a Rep coding region with at least one intron sequence inserted within the Rep coding region.

A helper function vector of the invention with a Rep coding region comprises at least one intron sequence inserted within the Rep coding region. The intron sequence can be a native intron sequence or a non-native intron sequence. In another embodiment, the Rep coding region comprising at lest one native intron sequence and at least one non-native intron sequence. The AAV Rep coding region of the AAV genome encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome.

A helper function vector of the invention with a Cap coding region comprises at least one intron sequence inserted within the Cap coding region. The intron sequence can be a native intron sequence or a non-native intron sequence. Embodiment, the Cap coding region comprises at least one native intron sequence and at least one non-native intron sequence. The AAV Cap coding region of the AAV genome encodes the capsid proteins VP1, VP2, and VP3, or functional homologues thereof. AAV helper functions can be introduced into the host cell by transfecting the host cell with an AAV helper construct either prior to, or concurrently with, the transfection of the AAV vector comprising the transgene.

AAV helper function constructs are used to provide at least transient expression of AAV Rep and/or Cap genes to complement missing AAV functions that are necessary for infectious AAV virion production. AAV helper function constructs lack AAV ITRs and can neither replicate nor package themselves. The AAV helper function constructs can be in the form of a plasmid, phage, transposon, cosmid, virus, or virion.

A number of AAV helper constructs have been described, such as the commonly used plasmids pAAV/Ad and pIM29+ 45 which encode both Rep and Cap expression products. (See, e.g., Samulski et al. (1989) *J. Virol.* 63:3822–3828; and McCarty et al. (1991) *J. Virol.* 65:2936–2945). A number of other vectors have been described which encode Rep and/or Cap expression products. See, e.g., U.S. Pat. No. 5,139,941. These AAV help constructs can be modified by inserting at least one intron sequence into the Rep and/or Cap coding region.

As a consequence of the infection of the host cell with a helper function, the AAV Rep and/or Cap proteins are produced. The Rep proteins also serve to duplicate the AAV genome. The expressed Cap proteins assemble into capsids, and the AAV genome is packaged into recombinant AAV virions. Recombinant AAV virions can be purified from the host cell using a variety of conventional purification methods, such as CsCl gradients. The resulting recombinant AAV virions are then ready for use for gene delivery to various cell types.

In one embodiment, the nucleic acid molecule encoding the Rep and Cap coding regions is present in the same construct, and at least one intron sequence can be inserted into one or more positions in the Rep coding region, Cap coding region, or both. In another embodiment, the Rep coding region is in a first construct and the Cap coding region in a second construct. At least one intron sequence can be inserted into the Rep coding region of the first construct, the Cap coding region of the second construct, or both the Rep coding region and Cap coding region in the first and second constructs.

In one embodiment of the invention a host cell comprising a Rep coding region can be transfected with a helper function vector comprising a Cap coding region without at least one intron sequence inserted within the Cap coding region. In another embodiment, the host cell comprises a Cap coding region can be transfected with a helper function vector comprising a Rep coding region with at least one intron sequence inserted within the Rep coding region.

Alternatively, the vector of the invention can be a virus other than a parvovirus, for example, replication defective retroviruses, adenoviruses and lentivirus. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ΨCrip, ΨCre, Ψ2 and ΨAm. The genome of adenovirus can be manipulated such that it encodes and expresses the transgene but is inactivated in terms of its ability to replicate in a normal lytic viral life cycle. See e.g., Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art.

A parvovirus helper function vector may be a plasmid, bacteriophage, transposon, cosmid, chromosome, artificial chromosome, virus, or other suitable genetic element, and may include selectable genetic markers such as antibiotic resistance genes. Such vectors may also include one or more accessory function genes, such as the E1A, E1B, E2A, VA RNA, and E4 regions of adenovirus.

The present invention further provides methods of using accessory function vectors to produce recombinant parvovirus and recombinant parvovirus virions. In certain embodiments, a method of the present invention includes the steps of introducing a parvovirus vector into a host cell; adding a parvovirus helper function vector of the present invention into the host cell; and culturing the host cell to produce recombinant parvovirus virions. The parvovirus vector and parvovirus helper function vector can be transfected into the host cell, either sequentially or simultaneously, using well-known techniques. In addition, accessory functions may also be added to the host cell. Accessory functions may be expressed in any of several ways, including infecting the host cell with a suitable helper virus (such as adenovirus, herpesvirus, or vaccinia virus), or by transfecting one or more accessory function vectors into the host cell.

Regulatory sequences required for gene expression, processing and secretion are art-recognized and are selected to direct expression of the desired protein in an appropriate cell. Accordingly, the term "regulatory sequence", as used herein, includes promoters, enhancers and other expression control elements. Such regulatory sequences are known and discussed in Goeddel,Gene expression Technology: Methods in Enzymology, p. 185, Academic Press, San Diego, Calif. (1990).

III Vectors

The vectors of the invention can be any vector suitable for delivering the nucleic and molecules of the invention into a suitable host cell. In a preferred embodiment, the invention uses adeno-associated viral vectors. AAV vectors can be constructed using known techniques to provide at least the operatively linked components of control elements including a transcriptional initiation region, a exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV ITR sequences.

The nucleotide sequences of AAV ITR regions are known. The ITR sequences for AAV-2 are described, for example by Kotin et al. (1994) *Human Gene Therapy* 5:793–801; Berns "Parvoviridae and their Replication" in Fundamental Virology, 2nd Edition, (B. N. Fields and D. M. Knipe, eds.) The skilled artisan will appreciate that AAV ITR's can be modified using standard molecular biology techniques. Accordingly, AAV ITR's used in the vectors of the invention need not have a wild-type nucleotide sequence, and may be altered, e.g., by the insertion, deletion or substitution of nucleotides. Additionally, AAV ITR's may be derived from any of several AAV serotypes, including but not limited to, AAV-1, AAV-2, AAV-3, AAV4, AAV-5, AAV-6, AAVX7, and the like. Furthermore, 5' and 3' ITR's which flank a selected nucleotide sequence in an AAV expression vector need not necessarily be identical or derived from the same AAV serotype or isolate, so long as the ITR's function as intended, i.e., to allow for excision and replication of the bounded nucleotide sequence of interest when AAV rep gene products are present in the cell.

The skilled artisan can appreciate that regulatory sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter Boshart et al. (1985) *Cell* 41:521–530, herpesvirus thymidine kinase (HSV-TK) promoter (McKnight et al. (1984) *Cell* 37: 253–262), β-actin promoters (e.g., the human β-actin promoter as described by Ng et al. (1985) *Mol. Cell Biol.* 5: 2720–2732) and colony stimulating factor-1 (CSF-1) promoter (Ladner et al. (1987) *EMBO J.* 6: 2693–2698).

Alternatively, the regulatory sequences of the AAV vector can direct expression of the transgene preferentially in a particular cell type, i.e., tissue-specific regulatory elements can be used. Non-limiting examples of tissue-specific promoters which can be used include, central nervous system (CNS) specific promoters such as, neuron-specific promoters (e.g., the neurofilament promoter; Byrne and Ruddle (1989) *Proc. Natl. Acad. Sci. USA* 86:5473–5477) and glial specific promoters (Morii et al. (1991) *Biochem. Biophys Res. Commun.* 175: 185–191).

The AAV vector harboring the transgene flanked by AAV ITRs, can be constructed by directly inserting the transgene into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al. (1988) *Molec. Cell. Biol.* 8:3988–3996; Vincent et al. (1990) Vaccines 90 (Cold Spring Harbor Laboratory Press); Carter (1992) *Current Opinion in Biotechnology* 3:533–539; Muzyczka (1992) *Current Topics in Microbiol. and Immunol.* 158:97–129; Kotin (1994) *Human Gene Therapy* 5:793–801; Shelling et al. (1994) *Gene Therapy* 1:165–169; and Zhou et al. (1994) *J. Exp. Med.* 179:1867–1875).

Several AAV vectors are available from the American Type Culture Collection ("ATCC") under Accession Numbers 53222, 53223, 53224, 53225 and 53226.

The AAV vectors can be transfected into a host cell (See Section IV below) with a helper function, e.g., a helper function plasmid (See Section II) and/or accessory functions to produce recombinant AAV virions.

IV Host Cells

In order to produce recombinant parvovirus virions, e.g., AAV virions, an AAV vector can be introduced into a suitable host cell comprising helper functions or co-transfected with a helper function vector using known techniques, such as by transfection. A number of transfection techniques are generally known in the art. See, e.g., Graham et al. (1973) *Virology,* 52:456, Sambrook et al. (1989) Molecular Cloning, a laboratory manual, Cold Spring Harbor Laboratories, N.Y., Davis et al. (1986) Basic Methods in Molecular Biology, Elsevier, and Chu et al. (1981) *Gene* 13:197. Particularly suitable transfection methods include calcium phosphate co-precipitation (Graham et al. (1973) *Virol.* 52:456–467), direct micro-injection into cultured cells (Capecchi (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transduction (Felgner et al. (1987) *Proc. Natl. Acad. Sci. USA* 84:7413–7417), and nucleic acid delivery using high-velocity microprojectiles (Klein et al. (1987) *Nature* 327:70–73).

Suitable host cells for producing recombinant AAV virions include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed.

In one embodiment, cells from the stable human cell line, 293 (readily available through, e.g., the ATCC under Accession No. ATCC CRL1573) are preferred in the practice of the present invention Particularly, the human cell line 293, which is a human embryonic kidney cell line that has been transformed with adenovirus type-5 DNA fragments (Graham et al. (1977) *J. Gen. Virol.* 36:59), and expresses the adenoviral E1A and E1B genes (Aiello et al. (1979) *Virology* 94:460). The 293 cell line is readily transfected, and provides a particularly convenient platform in which to produce recombinant AAV virions.

V. Pharmaceutical Compositions and Pharmaceutical Administration

The vector of the invention can be incorporated into pharmaceutical compositions suitable for administration to a subject. Typically, the pharmaceutical composition comprises the vector of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular or subcutaneous injection. In another embodiment, the vector is administered perorally. In the most preferred embodiment, the vector is delivered to a specific location using stereostatic delivery.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The vector of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems,* J. R. Robinson, ed., Marcel Dekker, Inc., New York, 1978.

The pharmaceutical compositions of the invention may include a "therapeutically effective amount" or a "prophylactically effective amount" of the vectors of the invention. A "therapeutically effective amount" refers to an amount effective, at dosages and for periods of time necessary, to achieve the desired therapeutic result. A therapeutically effective amount of the vector may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

Method and Materials (i) Plasmid Construction and DNA Manipulation

This example describes the construction of a plasmid comprising the introns. The 850 bp human β-globin intron 2 was amplified by PCR from human genomic DNA using primers 5' GTT TTG GGA CGT TTC CTG AGT CAG GTG AGT CTA TGG GAC CCT TGA TG 3' (SEQ ID NO: 1) and 5' CAG TTT TTC GCG AAT CTG TGG GAG GAA GAT AAG AGG TAT G 3' (SEQ ID NO: 2). The amplified intron was then cloned into pSub201 through PCR mediated mutagenesis at position 654. The resulting plasmid was named piAAVG850. The intron cloned into this position maintained the consensus sequence of splice donor site and splice acceptor site. The helper plasmid pCLR1 was cloned by swapping the SfiI-NruI of piAAV850 to pAd/AAV. The helper plasmids pCLR0, pCLR2, pCLV1, pCLV2 and pCLV3 were cloned in a similar way by inserting the 850 bp human β-globin intron into AAV genome at position 302, 1529, 2309, 2728, 2916 respectively. These sites correspond to the position in RNA for 5' untranslated region, Rep52/40, VP1, VP2, VP3. All these insertions maintained the consensus sequences for the splice donor sites and acceptor sites. To generate pCLR-C3 k, the human collagen intron was amplified by 5' CGG AGA AGC AGT GGA TCC AGG TGA GTA ATT GAC AAA GCC A 3' (SEQ ID NO: 3) and 5' GAT GTA TGA GGC CTG GTC CTC CTG TGA GCA AGA AGG AAG TG 3' (SEQ ID NO: 4) and then cloned into pAd/AAV at position number 1052. The 1.5 k, 2.0 k and 3.5 kbp Lamda DNA fragments (EcoRI/HindIII digestion) were cloned to the MfeI site in the β-globin intron in pCLR1 to generate pCLR1-1.5 k, pCLR1-2.0 k and pCLR1-3.5 k, respectively. All PCR reactions were performed using Expand Long Template PCR System (Roche) according to the manufacturer's instruction.

Genomic DNA was extracted from cells according to the protocol described in Current Protocol of Molecular Biology (Sambrook et al., supra). Specifically, the cells was harvested, washed 1× with PBS and digested with proteinsase K in the presence of 150 mM NaCl, 10 mM tris and 100 mM EDTA at 37° C. overnight. After extracting twice with phenol/chloroform, the DNA was precipitated with 2× volume ethanol and used for PCR analysis.

(ii) Packaging Protocol

To package the recombinant vectors, human embryonic 293 kidney cell lines were obtained from ATCC and maintained in Dulbecco's modified Eagle's medium (DMEM) supplemented with 10% fetal bovine serum, 100 μg/ml streptomycin and 100 U/ml penicillin (all purchased from Sigma). Cells were maintained in a humidified 37° C. incubator with 5 % $CO_2$. Transfections were carried out using lipofectAMIN or calcium phosphate precipitation. LipofectaMIN was purchased from GIBCO BRL. The transfections were performed as recommended by the manufactures. For transfection using calcium phosphate precipitation, the method was described by Xiao, et al. (1998) *J Virol* 72: 10222–10226.

(iii) Immunohistochemical Staining

To examine cells expressing β-galactosidase, the cells were fixed on plates by incubation for 5 minutes in ice-colded 2% formaldehyde and 0.2% gluteraldehyde in phosphate-buffered saline (PBS) After washing three times with PBS, the β-galactosidase activity was detected by staining for 4 hours in PBS containing 5 mM $K_4Fe(CN)_6$, 1 mM $MgCl_2$, and 1 mg/ml X-gal. The reaction was stopped by removing the staining solution and replaced with PBS containing 10% Glycerol.

(iv) Replication Competent AAV assay and Wild Type AAV Titer Determination

The infectious replication competent AAV or wild type AAV was assayed using a modified method described by Clark, et. al. ((1996) *Gene Ther* 3: 1124–1132). In detail, the AAV or recombinant AAV preparations in 10 fold dilutions was used infected 293 cells in the presence of adenovirus virus infection at MOI 10. The cells were harvested at 36 hours post-infection and genomic DNA was extracted. The amount of replication competent AAV (rcAAV) or wild-type AAV (wtAAV) was determined by PCR analysis of genomic for the presence AAV Rep region using primers 5' CCG TGG CCG AGA AGC TGC AGC GCG ACT TTC 3' (SEQ ID NO: 5) and 5' CCC CTC CTC CCA CCA GAT CAC CAT C 3' (SEQ ID NO: 6). The last dilution with positive signal was used to calculate the amount of infectious replication competent AAV and wild-type AAV particles.

AAV virion titer was determined by ELISA using Progen kit (Germany) (See Grimm, et al. (1999) *Gene Ther* 6: 1322–1330). The procedures were carried out as described by manufacturer. AAV genome titer was determined by dot blot. The procedures were described previously by Gao et al. ((1998) *Hum Gene Ther* 9: 2353–2362).

(v) rAAV Titer Determination

The rAAV infectious titer was determined using either GFP or lacZ as reporter gene. For rAAV-lacZ, each blue cell after X-Gal staining represents one infectious unit (LFU). For rAAV-GFP, each green cell under UV microscopy represents one infectious unit (GFU).

(vi) Western Blot

The harvested cells are lysed with RIPA buffer (10 mM tris pH 8.2, 1% Triton X-100, 1% SDS and 0.15M NaCl). About 10 μg of protein for each sample was eletrophoresed on 10% polyacrylamide gels. Proteins were transferred to nitro-cellulose membranes, and the Rep and capsid proteins were detected with anti-Rep(259.5) and anti-Cap monoclonal antibodies. All these antibodies were purchased from Research Diagnostics Inc (Flanders, N.J., USA). A ECL kit (Amersham) was used to develop final pictures.

Example 2

The Effect Additional Introns on AAV Packaging

This example demonstrates that the addition of non-native introns into a helper plasmid renders the AAV inefficient for packaging. In the wild type AAV genome, there is only a single native intron. The alternative splicing from this native intron gives rise to mRNA for Rep68, Rep40 and VP1. The small intron itself encodes amino-acid residues for Rep78 and Rep 52. Due to the size restraint of the AAV virion, non-essential introns can not be accommodated in the AAV genome.

Figure 1A:
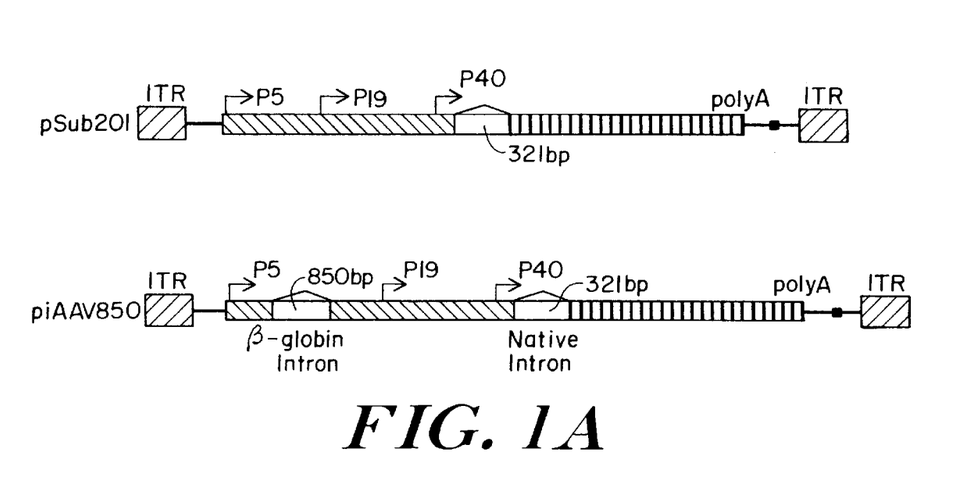
FIG. 1A is a schematic drawing of constructs for infectious clones, pSub201 with the native intron sequence and piAAV850 with the native intron sequence and a non-native intron sequence.

The 850 bp human β-globin intron was introduced into the AAV genome at position 654 (see FIG. 1A) and an infectious AAV clone, piAAV850 (i stands for intron), was obtained. This insertion was located in the coding region of the gene driven by the p5 promoter. Being downstream, it was predicted to have no effects on the transcripts from p19 and p40 promoters. The major effect by the addition of the non-native intron was to increase in the AAV genome size.

Human 293 cells were transfected with 5 μg of pSub201 or piAAV850 in the presence of adenovirus infection at MOI 10. The virus was harvested 48 hours post-infection and the virus titer was determined according to the experimental methods described in Example 1. The results from the AAV Rep and Cap gene expression profile of piAAV850 showed that it was almost identical to that of pSub201 (data not shown). The replication of AAV and piAAV850 was indistinguishable between piAAV850 and pSub201 (data not shown).

The packaged particles were assayed by ELISA and were found to be almost identical between pSub201 (referred to as wtAAV in Table 1) and piAAV850 (referred to as iAAV in Table 1). However, there were distinct differences in the genomic titer, as determined by dot blot analysis. The results showed that about 50 % of virus produced from pSub201 contained DNA, while less than 20% of virus generated from piAAV850 contained DNA.

A comparison of infectious particles revealed even more dramatic differences. One out of approximately one hundred virus particles generated from pSub201 was infectious and was capable of replication. However, less than one out of 10000 particles generated from piAAV850 was capable of replication. This data shows that the majority of particles generated from piAAV850, with the non-native intron sequence, were non-infectious defective particles and the ratio of infectious particles to physical particles decreased by 100 fold with an addition of 850 base pair β-globulin intron sequence.

TABLE 1

A comparison of wild type AAV generation from pSub201 and piAAV850.

| | Virion Titer pts/ml Elisa | Genome Titer genomes/ml dot blot | Infectious Titer IU/ml infectious assay | genomes/ pts | IU/pts |
|---|---|---|---|---|---|
| WtAAV | $2.7 \times 10^{12}$ | $1.35 \times 10^{12}$ | $2 \times 10^{10}$ | 50% | 1:135 |
| IAAV | $3.8 \times 10^{12}$ | $6.75 \times 10^{11}$ | $2 \times 10^{8}$ | 17.8% | 1:19000 |

Collectively, these results demonstrate that the overall AAV gene expression remains unchanged because the artificial intron is spliced out during translation. In addition, the oversized virus is less efficient for packaging and produces defective particles.

Example 3

Helper Plasmids with Introns Support rAAV Production

Figure 1B:
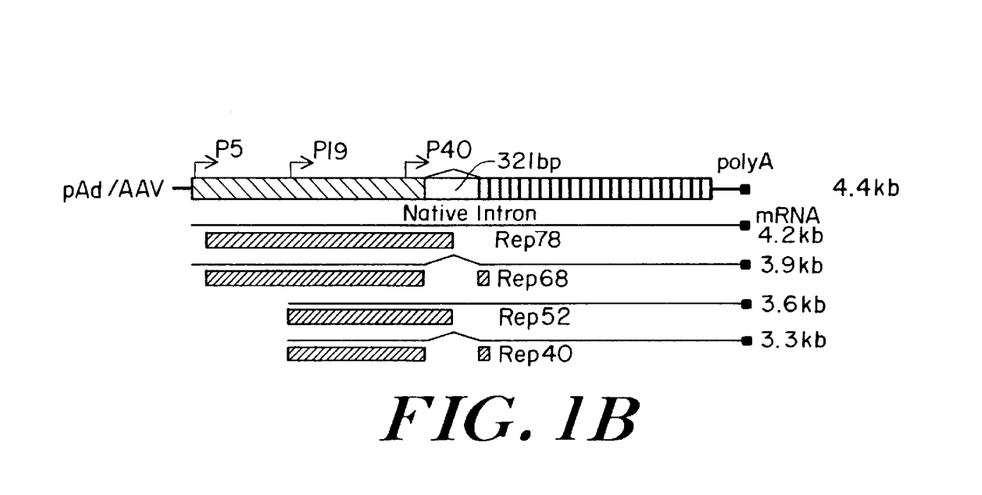
FIG. 1B is a schematic drawing of the pAd/AAV helper plasmid construct without inverted terminal repeat sequences.
Figure 1C:
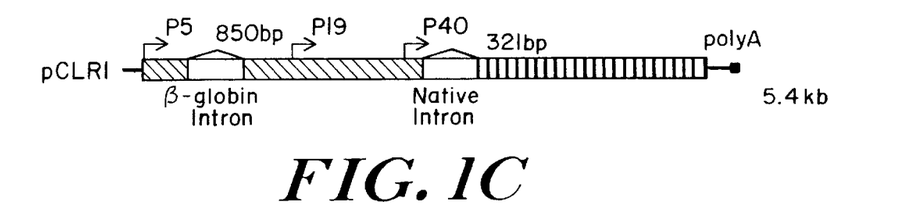
FIG. 1C is a schematic construct of the helper plasmid pCLR1 with a native intron sequence and a non-native β-globin intron sequence.
Figure 1D:
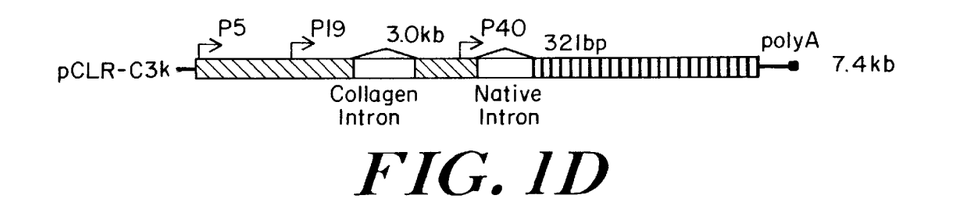
FIG. 1D is a schematic construct of the helper plasmid pCLR-3 k with a native intron sequence and a non-native collagen intron sequence.
Figure 1E:
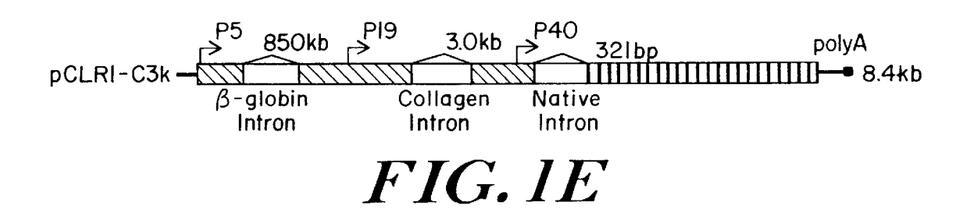
FIG. 1E is a schematic construct of the helper plasmid pCLR1-3 k with a native intron sequence, a non-native β-globin intron sequence and a non-native collagen intron sequence.

To demonstrate that the helper plasmids consisting the non-native sequences support recombinant AAV production, the different helper plasmid constructs were transfected with AAV into the human 293 cell line. The adenovirus helper plasmid was used as a control. Helper plasmids for rAAV production with non-native introns were constructed as shown in FIG. 1B and Table 2. The plasmid pCLR1 carried one human β-globin intron. The pCLR1-1.5 k, pCLR1-2.0 k and pCLR1-3.0 k carried the same β-globin intron with additional phage DNA sequences inserted within the intron. The size of the DNA sequences were 1.5 kb, 2.0 kb and 3.0 kb, respectively. The DNA sequences were used to increase the size of the intron. Plasmid pCLR-3 k carried the 3.0 kb human collagen intron in p19 transcripts. The pCLR1-C3 k carried both the β-globin intron and the collagen intron. These helper plasmids were then examined for their ability to support rAAV production by transfection into 293 cell lines with each helper plasmid, vector plasmid and adenovirus helper plasmid in ratio of 1:1:2. The virus was harvested 96 hours post-transfection and equal amount of fraction was used to infect 293 cells in presence of adenovirus infection at MOI 10 to determine the rAAV titer. The titer was reported as LFU/field under microscopy and as GFU/field under UV microscopy.

TABLE 2

A summary of intron insertions into helper plasmids and their corresponding positions

| Helper | Intron insertion | Position | Size of insertion | Size of helper |
|---|---|---|---|---|
| pAD/AAV | none | N/A | 0.00kb | 4.40kb |
| pCLR1 | β-globin (850bp) | nt 654 (rep78/68) | 0.85kb | 5.25kb |
| pCLR1-1.5k | β-globin + 1.5kb λDNA | nt 654 (rep78/68) | 2.35kb | 6.75kb |
| pCLR1-2.0k | β-globin + 2.0kb λDNA | nt 654 (rep78/68) | 2.85kb | 7.25kb |
| pCLR1-3.5k | β-globin + 3.5kb λDNA | nt 654 (rep78/68) | 4.35kb | 8.75kb |
| pCLR-C3k | Collagen (3.0kb) | nt 1052 (rep52/40) | 3.00kb | 7.40kb |
| pCLR1-C3k | β-globin/ collagen | nt 654 (rep78/68) nt 1052 (rep52/40) | 3.85kb | 8.25kb |

Figure 2A:
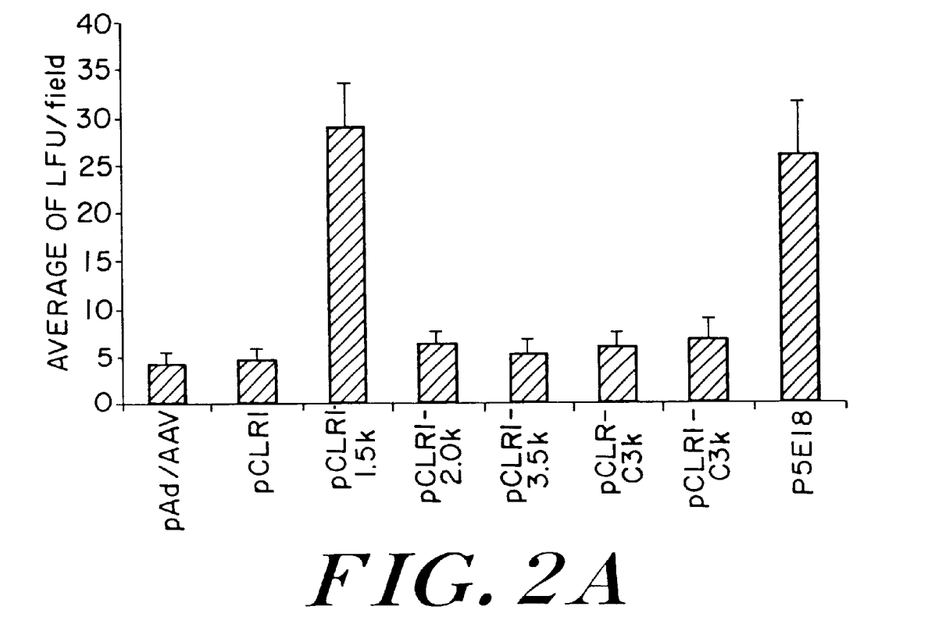
FIG. 2A is a graph comparing the recombinant AAV virion yield using various helper plasmids. Human 293 cells were transfected with each helper plasmid, an AAV vector and adenovirus helper plasmid in ratio of 1:1:2. The titer is shown as LFU/field under microscopy.
Figure 2B:
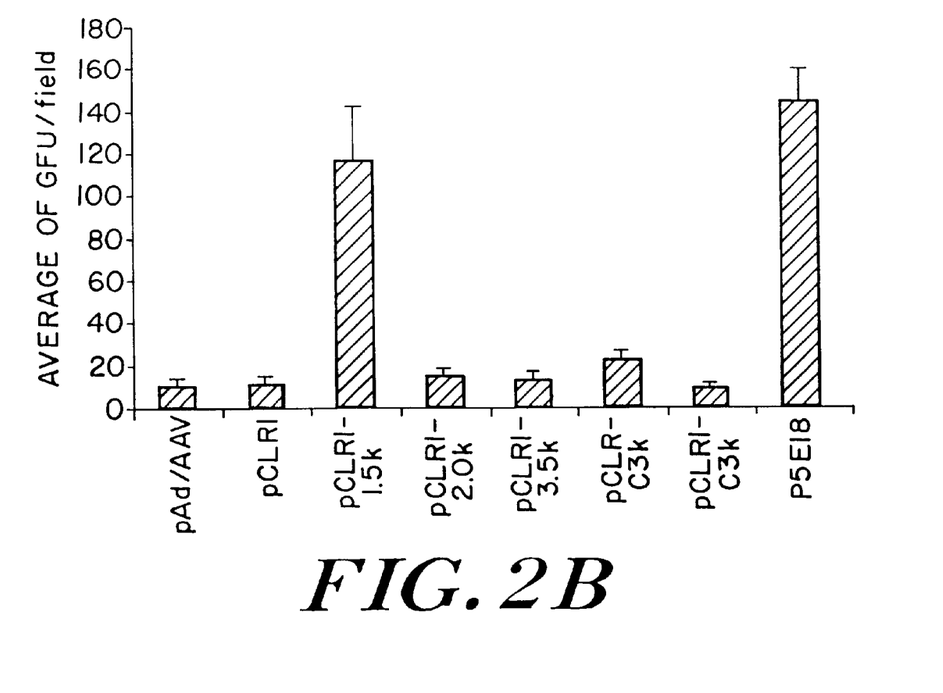
FIG. 2B is a graph comparing the recombinant AAV virion yield using various helper plasmids. Human 293 cells were transfected with each helper plasmid, vector plasmid and adenovirus helper plasmid in ratio of 1:1:2. The titer was reported as GFU/field under UV microscopy.

The results from these experiments are presented in FIG. 2A and FIG. 2B. Each helper plasmid was analyzed using two reporter vector plasmids, rAAV-CMV-lacZ and rAAV-CMV-GFP. The results demonstrate that the new helper plasmids were as least as efficient in supporting rAAV production as the original helper plasmid pAd/AAV.

Example 3

Reduction Replicatio Competent AAV (rcAAV) Particles

This experiment demonstrates the reduction in the number of replication competent virions produced using helper plasmids with non-native intron sequences. The increase in size of the helper plasmids results in a decrease in AAV packaging effiency, thereby reducing the generation of rcAAV particles.

The amount of rcAAV particles in the rAAV preparations was assayed as described in Example 1. Approximately 1/10 of the vector preparation from $10^7$ cells (there were ~$1 \times 10^{10}$ rAAV particles) was used to infect 293 cells in the presence of helper adenovirus infection at a MOI of 10. The genomic DNA of the cells was extracted at 36 hours post adenovirus and rAAV infection. The replicated rcAAV genome was detected by PCR amplification analysis.

The results are summarized in Table 3 below, which shows that the rAAV vector produced by pAd/AAV generated detectable rcAAV at a 1 to 100 dilution. However, none of the helper plasmids with additional non-native introns produced detectable rcAAV even at a 1 to 10 dilution. The helper plasmid p5E18 also generated detectable rcAAV at dilution of 1:10 but not 1:100. Plasmid p5E18, it contains a 3.0 kb spacer fragment between p5 promoter and Rep initiation codon 20. rcAAV could still be detected in rAAV preparations generated using p5E18 as helper plasmid, although at a 10 fold lower amount than that of pAd/AAV. Thus, reversion mutants, (that replicate rcAAV) were still easily generated even with p5E18 as helper plasmid. This spacer reduced the generation of rcAAV but did not completely eliminate it. This is the key factor leading to the rcAAV reduction.

TABLE 3

Replication competent AAV (rcAAV) contamination in rAAV preparation using various helper plasmids.

| Helper Plasmid | rcAAV @1:10 | rcAAV @1:100 | rcAAV @1:1000 |
|---|---|---|---|
| pAd/AAV | + | + | − |
| pCLR1 | − | − | − |
| pCLR1-1.5k | − | − | − |
| pCLR1-2.0k | − | − | − |
| pCLR1-3.5k | − | − | − |
| pCLR-C3k | − | − | − |
| pCLR1-C3k | − | − | − |
| p5E18 | + | − | − |

Example 4

Improved rAAV Yield Using Helper Plasmids with Non-native Intron Sequences

Figure 3A:
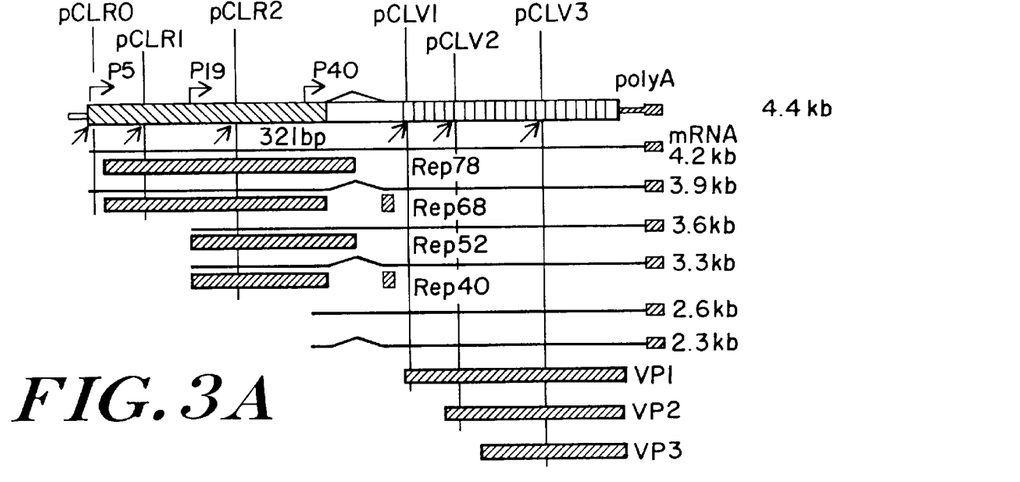
FIG. 3A is a schematic drawing of constructs the position of additional non-native introns relative to AAV genome.
Figure 3B:
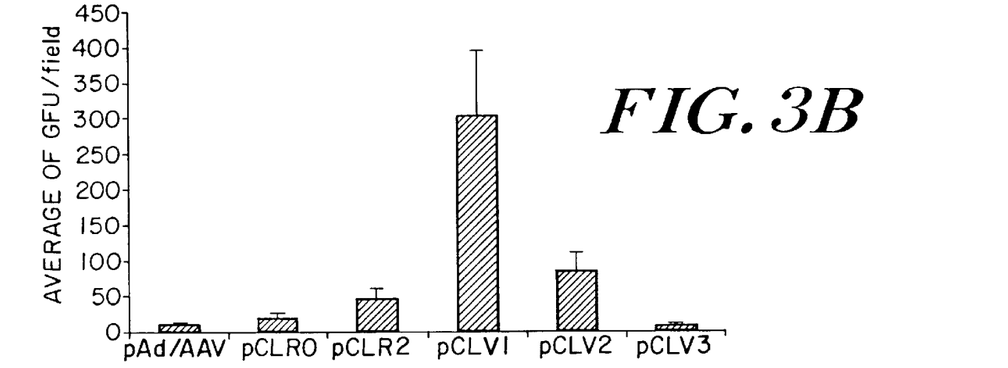
FIG. 3B is a graph comparing the recombinant AAV virion titer using various helper plasmids and GFP as reporter gene.
Figure 3C:
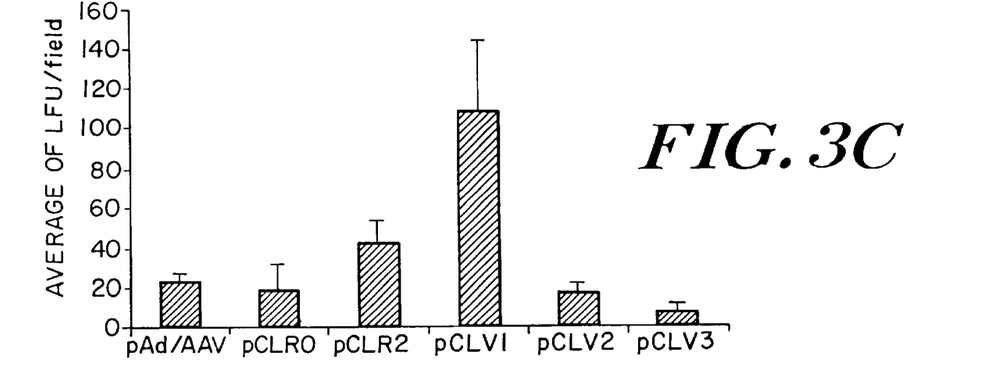
FIG. 3C is a graph comparing the recombinant AAV virion titer using various helper plasmids and LacZ as reporter gene.

This example demonstrates the improved yield of rAAV obtained using helper plasmids with non-native sequences. The experiments investigated the effect of the introns in regulating the rep and cap gene expression by inserting the human β-globin at various positions in AAV genome. These helper plasmids with introns in different positions are shown in FIG. 3A. The results from the experiments are shown in FIGS. 3B and C and show that all the helper plasmids were capable of supporting rAAV production using either lacZ or GFP as reporter gene. The rAAV yield using pCLR1-1.5 k and pCLV1 as a helper plasmid was considerably higher than that obtained with other helper plasmids (FIG. 2 and FIG. 3). The increase of rAAV titer was about 5 to 7 fold.

Figure 4:
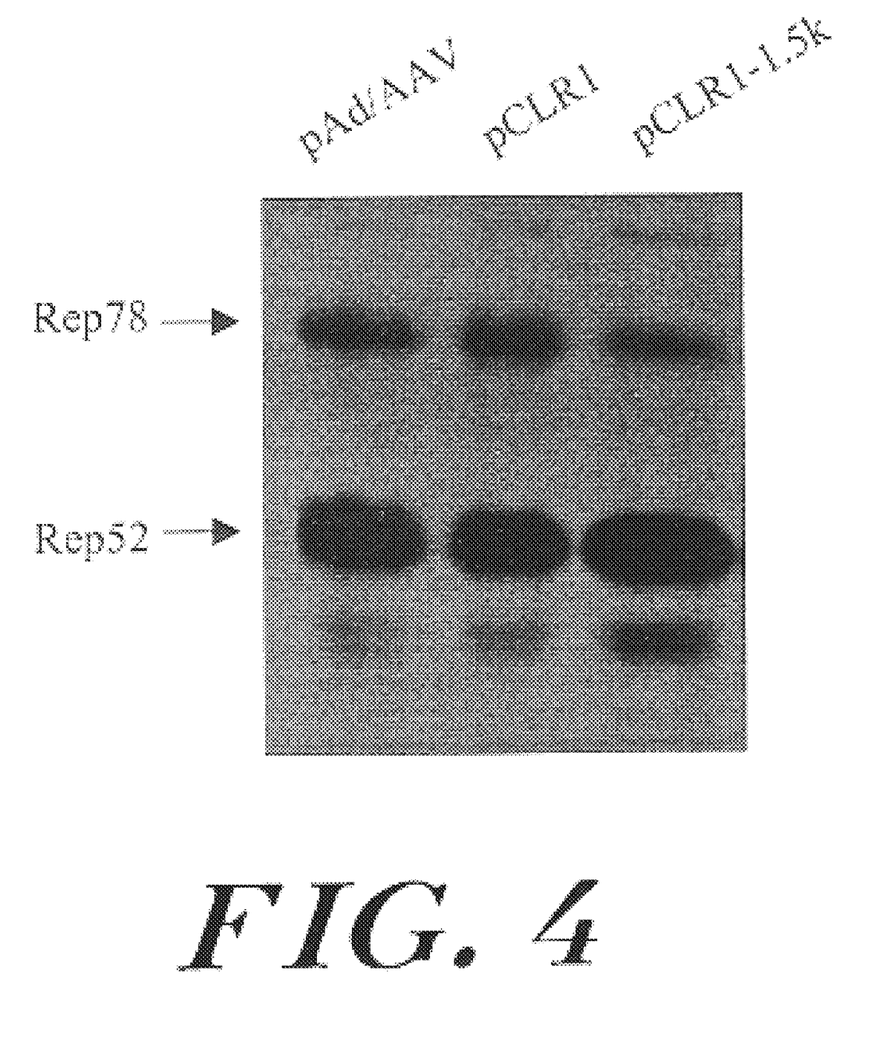
FIG. 4 is a photograph of a Western blot shaving Rep gene expression from the pCL1-1.5 k helper plasmid, and Cap gene expression from pCLV1 helper plasmid with pAd/AAV being used as positive control

A Western blot analysis of Rep gene expression from pCL1-1.5 k, Cap gene expression from pCLV1 with pAd/AAV used as positive control, is shown in FIG. 4. The results from the Western blot analysis revealed that there was an increased ratio of Rep52/40 to Rep 78/68 in pCLR1-1.5 k. For pCLV1, there was an increase in rAAV titer.

Collectively, these results demonstrate that in the AAV infectious clone, intron insertion does not affect the properties of Rep proteins expressed. Normal levels of both Rep and Cap proteins were expressed and the replication of the AAV genome was not impaired. However, the production of infectious rcAAV particles was greatly reduced due to the oversized AAV genome caused by the insertion of the artificial intron. Moreover, the rAAV packaging was significantly more efficient with the helper plasmid containing the non-native introns than that obtained using the original helper plasmid. In addition, non-native intron insertions into helper plasmids improve the yield of rAAV produced.

EQUIVALENTS

Those skilled in the art will recognize, or be able to ascertain using no more than routine experimentation, numerous equivalents to the specific methods and reagents described herein. Such equivalents are considered to be within the scope of this invention and are covered by the following claims.

What is claimed is:

1. A nucleic acid molecule encoding an adeno-associated virus (AAV) helper function, said nucleic acid molecule comprising:
   a Rep coding region derived from an AAV;
   a Cap coding region derived from an AAV; and
   at least one intron sequence inserted at one or more positions within the Cap coding region and the Rep coding region, such that the intron sequence increases the size of the nucleic acid molecule to a size larger than a nucleic acid molecule without the intron sequence, wherein the increase in size prevents packaging of a pseudo wild-type AAV into a replication competent particle.

2. The nucleic acid molecule of claim 1, wherein the AAV is selected from the group consisting of AAV-1, AAV-2, AAV-3, AAV4, AAV-5 and AAV-6.

3. The nucleic acid molecule of claim 1, wherein the intron sequence is an native intron sequence.

4. The nucleic acid molecule of claim 2, wherein the AAV is AAV-2.

5. The nucleic acid molecule of claim 4, wherein the intron sequence is an non-native intron sequence.

6. The nucleic acid molecule of claim 5, wherein the non-native intron sequence is selected from the group consisting of α-globulin intron, β-globulin intron, collagen intron, ovalbumin intron, SV40 intron and p53 intron.

7. The nucleic acid molecule of claim 3, wherein the native intron sequence is an AAV intron sequence.

8. A nucleic acid molecule encoding an adeno-associated virus (AAV) helper function, said nucleic acid molecule comprising:
   a Cap coding region derived from an AAV; and
   at least one intron sequence inserted at one or more positions within the Cap coding region, such that the intron sequence increases the size of the nucleic acid molecule to a size larger than a nucleic acid molecule without the intron sequence wherein the increase in size prevents packaging of a pseudo wild-type AAV into a replication competent particle.

9. The nucleic acid molecule of claim 8, wherein the AAV is selected from the group consisting of AAV-1, AAV-2, AAV-3, AAV4, AAV-5 and AAV-6.

10. The nucleic acid molecule of claim 8, wherein the intron sequence is a non-native intron sequence.

11. The nucleic acid molecule of claim 8, wherein the intron sequence is a native intron sequence.

12. The nucleic acid molecule of claim 9, wherein the AAV is AAV-2.

13. The nucleic acid molecule of claim 10, wherein the non-native intron sequence is selected from the group consisting of α-globulin intron, β-globulin intron, collagen intron, ovalbumin intron, SV40 intron and p53 intron.

14. The nucleic acid molecule of claim 11, wherein the native intron sequence is an AAV intron sequence.

15. A nucleic acid molecule encoding an adeno-associated virus (AAV) helper function, said nucleic acid molecule comprising:
   a Rep coding region derived from an AAV; and
   at least one intron sequence inserted at one or more positions within the Rep coding region, such that the intron sequence increases the size of the nucleic acid molecule to a size greater than a nucleic acid molecule without the intron sequence, wherein the increase in size prevents packaging of a pseudo wild-type AAV into a replication competent particle.

16. A helper function vector comprising the nucleic acid molecule of any one of claims 1, 8, or 15.

17. A host cell comprising the nucleic acid molecule of any one of claims 1, 8, or 15.

18. The nucleic acid molecule of claim 15, wherein the AAV is selected from the group consisting of AAV-1, AAV-2, AAV-3, AAV4, AAV-5 and AAV-6.

19. The nucleic acid molecule of claim 15, wherein the intron sequence is an non-native intron sequence.

20. The nucleic acid molecule of claim 15, wherein the intron sequence is an native intron sequence.

21. The nucleic acid molecule of claim 18, wherein the AAV is AAV-2.

22. The nucleic acid molecule of claim 19, wherein the non-native intron sequence is selected from the group consisting of α-globulin intron, β-globulin intron, collagen intron, ovalbumin intron, SV40 intron and p53 intron.

23. The nucleic acid molecule of claim 20, wherein the native intron sequence is an AAV intron sequence.

24. The helper function vector of claim 16, wherein the vector is a plasmid.

25. The helper function vector of claim 16, wherein the vector is selected from the group consisting of adenovirus, herpesvirus and baculovirus.

26. A method of producing recombinant AAV virions comprising:

introducing a AAV vector into a host cell;

adding a helper function vector into the host cell, wherein the helper function vector comprises a nucleic acid molecule with a Cap coding region and a Rep coding region derived from an AAV, and at least one intron sequence inserted at one or more positions in the Cap coding region and the Rep coding region, such that the intron sequence increases the size of the nucleic acid molecule to a size larger than a nucleic acid molecule without the intron sequence, wherein the increase in size prevents packaging of a pseudo wild-type AAV into a replication competent particle; and culturing the host cell to produce recombinant AAV virions.

27. The method of claim 26, wherein the AAV vector is selected from the group consisting of AAV-1, AAV-2, AAV-3, AAV-4, AAV-5 and AAV-6.

28. The method of claim 26, wherein the helper function vector comprises a nucleic acid molecule with a Cap coding region and a Rep coding region derived from an AAV selected from the group consisting of AAV-1, AAV-2, AAV-3, AAV-4, AAV-5 and AAV-6.

29. The method of claim 26, wherein the intron sequence is a non-native intron sequence.

30. The method of claim 26, wherein the non-native intron sequence is selected from the group consisting of α-globulin intron, β-globulin intron, collagen intron, ovalbumin intron, SV40 intron and p53 intron.

31. The method of claim 26, wherein the intron-sequence is a native intron sequence.

32. The method of claim 26, wherein the helper function vector is selected from the group consisting of a plasmid, phage, transposon, cosmid, and virus.

33. The method of claim 31, wherein the native intron-sequence is an AAV intron sequence.

34. A method of producing recombinant AAV virious comprising:

introducing an AAV vector into a host cell;

adding a first helper function vector into the host cell, wherein the first helper function vector comprises a nucleic acid molecule encoding an AAV region selected from the group consisting of a Cap coding region and a Rep coding region, and at least one intron sequence inserted in at least one position within said regions, such that the intron sequence increases the size of the nucleic acid molecule to a size larger than a nucleic acid molecule without the intron sequence, wherein the increase in size prevents packaging of a pseudo wild-type AAV into a replication competent particle; and culturing the host-cell to produce recombinant AAV virions.

35. The method of claim 34, further comprising introducing a second helper function vector into a host cell, wherein the second helper function vector comprises a nucleic acid molecule encoding an AAV region selected from the group consisting of a Cap coding region and a Rep coding region, wherein the second helper function vector is different from the first helper function vector.

36. The method of claim 34, further comprising introducing a second helper function vector into a host cell, wherein the second helper function vector comprises a nucleic acid molecule encoding an AAV region selected from the group consisting of a Cap coding region and a Rep coding region, and an intron sequence inserted in at least one position in said regions, wherein the second helper function vector is different from the first helper function vector.

37. The method of claim 34, wherein the AAV vector is selected from the group consisting of AAV-1, AAV-2, AAV-3, AAV4, AAV-5 and AAV6.

38. The method of claim 34, wherein the first helper function vector comprises a nucleic acid molecule encoding an AAV region derived from an AAV selected from the group consisting of AAV-1, AAV-2, AAV-3, AAV4, AAV-5 and AAV-6.

39. The method of claim 34, wherein the first helper function vector is selected from the group consisting of a phage, transposon, cosmid, and virus.

40. The method of claims 34, 35 and 36, wherein the intron sequence is a non-native intron sequence.

41. The method of claims 34, 35, and 36, wherein the intron sequence is a native intron sequence.

42. The method of claims 35 and 36, wherein the second helper function vector comprises a nucleic acid molecule encoding an AAV region derived from an AAV selected from the group consisting of AAV-1, AAV-2, AAV-3, AAV-4, AAV-5 and AAV-6.

43. The method of claims 35 and 36, wherein the second helper function vector is selected from the group consisting of a phage, transposon, cosmid, and virus.

44. The method of claim 40, wherein the non-native intron sequence is selected from the group consisting of α-globulin intron, β-globulin intron, collagen intron, ovalbumin intron, SV40 intron and p53 intron.

45. The method of claim 41, wherein the native intron sequence is an AAV intron sequence.

* * * * *

SEQUENCE LISTING

<160> NUMBER OF SEQ ID NOS:  6

<210> SEQ ID NO 1
<211> LENGTH: 47
<212> TYPE: DNA
<213> ORGANISM: Homo sapiens

<400> SEQUENCE: 1
gttttgggac gtttcctgag tcaggtgagt ctatgggacc cttgatg          47

<210> SEQ ID NO 2
<211> LENGTH: 40
<212> TYPE: DNA
<213> ORGANISM: Homo sapiens

<400> SEQUENCE: 2
cagtttttcg cgaatctgtg ggaggaagat aagaggtatg              40

<210> SEQ ID NO 3
<211> LENGTH: 40
<212> TYPE: DNA
<213> ORGANISM: Homo sapiens

<400> SEQUENCE: 3
cggagaagca gtggatccag gtgagtaatt gacaaagcca              40

<210> SEQ ID NO 4
<211> LENGTH: 41
<212> TYPE: DNA
<213> ORGANISM: Homo sapiens

```
<400> SEQUENCE: 4
gatgtatgag gcctggtcct cctgtgagca agaaggaagt g                                41

<210> SEQ ID NO 5
<211> LENGTH: 30
<212> TYPE: DNA
<213> ORGANISM: adeno-associated virus 2

<400> SEQUENCE: 5
ccgtggccga gaagctgcag cgcgactttc                                             30

<210> SEQ ID NO 6
<211> LENGTH: 25
<212> TYPE: DNA
<213> ORGANISM: adeno-associated virus 2

<400> SEQUENCE: 6
cccctcctcc caccagatca ccatc                                                  25
```